US007306649B2

(12) United States Patent
Boyle et al.

(10) Patent No.: US 7,306,649 B2
(45) Date of Patent: Dec. 11, 2007

(54) 3D MINIATURE PRECONCENTRATOR AND INLET SAMPLE HEATER

(75) Inventors: Paul Boyle, London (GB); David Ruiz-Alonso, Cambridge (GB); Andrew Koehl, Cambridge (GB); Martyn Rush, Cambridge (GB); Russell Parris, Cambridge (GB); Ashley Wilks, Cambridge (GB)

(73) Assignee: Advance Nanotech, Inc., New York, NY (US)

( * ) Notice: Subject to any disclaimer, the term of this patent is extended or adjusted under 35 U.S.C. 154(b) by 251 days.

(21) Appl. No.: 11/239,367

(22) Filed: Sep. 30, 2005

(65) Prior Publication Data

US 2007/0084347 A1    Apr. 19, 2007

(51) Int. Cl.
*B01D 53/02* (2006.01)

(52) U.S. Cl. .................. 95/82; 95/89; 96/101; 96/105; 73/23.41; 436/177

(58) Field of Classification Search .................... 95/82, 95/85, 89; 96/101, 105, 108, 413; 73/23.35, 73/23.37, 23.41, 23.42; 422/83–98; 436/161, 436/177, 178; 210/656, 198.2
See application file for complete search history.

(56) References Cited

U.S. PATENT DOCUMENTS

| | | | | |
|---|---|---|---|---|
| 5,481,110 A * | 1/1996 | Krishnaswamy et al. | ... | 250/288 |
| 5,637,135 A * | 6/1997 | Ottenstein et al. | ............ | 96/101 |
| RE36,350 E * | 10/1999 | Swedberg et al. | ....... | 210/198.2 |
| 5,970,803 A * | 10/1999 | Staples et al. | .......... | 73/863.12 |
| 6,171,378 B1 * | 1/2001 | Manginell et al. | ............ | 96/143 |
| 6,455,003 B1 * | 9/2002 | Anvia et al. | ................... | 422/88 |
| 6,527,835 B1 * | 3/2003 | Manginell et al. | ............ | 96/102 |
| 6,575,014 B2 * | 6/2003 | Lo et al. | ..................... | 73/23.41 |
| 6,656,738 B1 * | 12/2003 | Vogel et al. | ................. | 436/161 |
| 6,914,220 B2 * | 7/2005 | Tian et al. | .................. | 219/408 |
| 6,966,212 B2 * | 11/2005 | Klee et al. | ................. | 73/23.41 |
| 7,118,712 B1 * | 10/2006 | Manginell et al. | .......... | 422/101 |
| 7,122,152 B2 * | 10/2006 | Lewis et al. | ................... | 422/50 |
| 7,168,298 B1 * | 1/2007 | Manginell et al. | ......... | 73/54.25 |
| 2002/0178785 A1 * | 12/2002 | Lo et al. | ..................... | 73/23.41 |
| 2004/0056016 A1 * | 3/2004 | Tian et al. | .................. | 219/408 |
| 2004/0171169 A1 * | 9/2004 | Kallury et al. | .............. | 436/178 |
| 2005/0223775 A1 * | 10/2005 | Klee et al. | ................. | 73/23.41 |
| 2006/0053905 A1 * | 3/2006 | Klee et al. | ............... | 73/863.11 |
| 2006/0101924 A1 * | 5/2006 | Klee et al. | ............... | 73/863.12 |

* cited by examiner

*Primary Examiner*—Duane Smith
*Assistant Examiner*—Robert A Clemente
(74) *Attorney, Agent, or Firm*—Morgan, Lewis & Bockius LLP

(57) ABSTRACT

The present invention relates to a three dimensional preconcentrator and inlet heater. The preconcentrator consists of a substrate with passageways, a conductive material coated to the top and the bottom of the substrate and an adsorbent coating covering the entire substrate. This substrate is suspended in a holding frame by a connecting bridge. The preconcentrator may also include a resistor and a proportional-integral-differential controller. The device may be used inline with a detector and can be retrofitted to existing devices. An array of preconcentrators may also be formed. The invention also relates to methods of use of the preconcentrator and methods of manufacture. A method of use includes contacting an analyte and a preconcentrator, allowing the analyte to adsorb to the preconcentrator and then desorbing the analyte. A method of manufacture involves applying the adsorbent coating by misted chemical deposition.

26 Claims, 5 Drawing Sheets

3D MINIATURE PRECONCENTRATOR AND INLET SAMPLE HEATER

FIELD OF THE INVENTION

The present invention relates to a preconcentrator and inlet sample heater for an analytical instrument. More particularly, the present invention relates to a micro-machined preconcentrator and inlet sample heater with a three-dimensional structure, integral heating, and a semiconductor substrate.

BACKGROUND OF THE INVENTION

In analytical chemistry, preconcentrators have been used for many years to collect molecules that are present in low concentrations. Analytical instruments may not be able to detect molecules in such low concentrations. Preconcentrators accumulate and concentrate one or more chemical species of interest over time, so that the analytical instruments can detect the molecule. Thus, preconcentrators increase the sensitivity of analytical techniques such as, e.g., gas chromatography, mass spectrometry, and ion mobility spectrometry (IMS).

Preconcentrators are particularly useful to aid in the detection of trace compounds such as drugs, explosives, and other toxic agents. As these compounds are typically found in the field, battery-powered portable detectors have been developed.

The key feature of a preconcentrator is the ability to adsorb an analyte and then release it at a specific temperature. To adsorb the analyte, special materials called adsorbent resins have been developed. Adsorbent resins are typically high surface area powders and the nature of the analyte determines the choice of resin.

Existing preconcentrators usually consist of an adsorbent 'slug' inside a tube. The sample passes through the tube and analytes adsorb onto the slug. When enough analyte has accumulated, the slug is heated to release a concentrated 'plume' of analyte into the detector for techniques such as e.g. IMS. These preconcentrators have a low surface area to volume ratio, requiring a long time to accumulate a sufficient quantity of analyte. Furthermore, due to a pressure drop across the preconcentrator, inline use with existing detectors may require changing the internal air handling. Such changes can be difficult, expensive and even preclude retrofitting of preconcentrators to an existing device. The slug is also large requiring a fair amount of time and energy to release the analyte. This energy consumption poses a particular problem when preconcentrators are used in portable detection systems as it lowers the battery life.

For portable systems, micro-machined preconcentrators have been designed. Typical inline micro-machined preconcentrators consist of a thin film serpentine structure with an adsorbent coating on top. The structure can have thickness in the order of microns and consequently is quite fragile. The heating element is external to the device, limiting thermal efficiency. A break in the structure, which also serves as the heating track, will ordinarily cause complete failure.

The surface area of such concentrators is essentially the surface area of the top of the structure, as the thickness is negligible. As a result, such devices have a relative low surface area to which the analyte adsorbs. Furthermore, because of their low surface area it takes a longer time to preconcentrate the analyte. Once sufficient analyte has accumulated, current is passed through the structure and causes desorption. Since the heating of the preconcentrator is often not uniform, additional time and energy are required to desorb the analyte. Furthermore, due to the non-uniform heating, it is difficult to accurately control desorption of the analyte.

Micro-machined preconcentrators may be mounted inline to the detector or externally. In an external preconcentrator, the preconcentrator located inside a chamber and the analyte enters through an inlet port and leaves through an outlet port. Such preconcentrators are disadvantageous in that they add complexity to the apparatus and thus hinder further miniaturization.

U.S. Pat. No. 6,239,428 to Kant discloses systems and methods of ion mobility spectrometry. The system may contain a preconcentrator whose temperature is modulated between two temperatures. The preconcentrator has permeable organic membranes or thin metal foils. Consequently, the preconcentrator has low surface area and is quite fragile.

U.S. Pat. No. 6,171,378 to Manginelli et al. is illustrative of a micro-machined external preconcentrator. The preconcentrator contains a substrate with a suspended membrane, which serves to support two resistive heating elements on top of which an adsorbent coating is deposited. Again, this preconcentrator does not maximize the surface area.

During the manufacture of a micro-machined preconcentrator, preconcentration material is placed on the device. One way to deposit the preconcentration material is to use ink jet deposition. This process employs about 70,000 individual drops and is slow and serial. Ink jet deposition lacks resolution to create ultra-small geometries and when complex features have to be printed, it can be prohibitively expensive.

There remains a need for a preconcentrator that does not create a large pressure drop, requires little energy to heat, can be micro-machined and improves the preconcentration abilities. There also remains a need for a cheap, efficient, and accurate method of manufacture of a micro-machined preconcentrator.

SUMMARY

Accordingly, one aspect of the present invention is directed to a preconcentrator that substantially obviates one or more of the problems due to the limitations and disadvantages of the related art.

Additional features and advantages of the invention are set forth in the description, which follows, and will be apparent, in part, from the description, or may be learned by practice of the invention. Certain objectives and other advantages of the invention will be realized and attained by the structure particularly pointed out in the written description and claims hereof, as well as the appended drawings.

A preconcentrator according to the instant disclosure illustratively comprises: a substrate with passageways therethrough; a conductive material, such as a metal, covering the top and bottom of the substrate; a top electrical lead connected to the material on the top of the substrate; a bottom electrical lead connected to the material on the bottom of the substrate; an adsorbent coating disposed on top and bottom of the material and along the inside of the passageways. The preconcentrator may also include a holding frame; and a connecting bridge connecting the substrate to the holding frame. The three-dimensional structure of the preconcentrator can advantageously create a large surface area to which an analyte may adsorb. Furthermore, the preconcentrator can have an integral heating element and a low thermal mass, making it ideal for battery operation.

The substrate, holding frame and connecting bridge can be silicon. The adsorbent coating can be polydimethylsiloxane (PDMS). In one embodiment of the invention, the preconcentrator is placed inline with a detector. In another embodiment, the preconcentrator is used as an inlet heater.

The preconcentrator may optionally include a temperature-variable resistor for temperature sensing. When the preconcentrator has such a resistor, a proportional-integral-differential controller may be used to control the preconcentrator temperature.

When used for retrofitting, the preconcentrator further includes a support. This support may contain a structural polymer such as TEFLON(R), ceramic or polyetheretherketone (PEEK).

One embodiment of the invention includes an array preconcentrator, which contains at least two coated substrates connected to each other by a connecting bridge with all substrates sharing the same holding frame. Each coated substrate typically includes passageways therethrough, a coating (e.g. metal) on the top and bottom of the substrate, and an adsorbent coating covering the substrate and electrical leads. In this array, optionally each coated substrate may selectively adsorb a different analyte of interest. The substrate, holding frame and connecting bridge may advantageously contain silicon.

Another embodiment of the invention is a method of preconcentrating an analyte comprising the steps of contacting the analyte and a preconcentrator, adsorbing the analyte to the adsorbent coating of the preconcentrator at a temperature and for a period of time sufficient to allow the analyte to adsorb, and releasing the analyte from the adsorbent coating. The preconcentrator may contain: a substrate with passageways therethrough; a conductive material covering the top and bottom of the substrate; a top electrical lead connected to the conductive material covering the top of the substrate; a bottom electrical lead connected to the conductive material covering the bottom of the substrate; and an adsorbent coating on top of the conductive material and along the inside of the passageways. The preconcentrator may also include a holding frame; and a connecting bridge connecting the substrate to the holding frame. The preconcentrator may be mounted inline with the detector. The substrate may include silicon. Optionally, the preconcentrator may further contain a temperature-variable resistor or a resistor and a proportional-integral-differential controller.

In one embodiment of the method of preconcentration, the step of contacting the analyte with the preconcentrator comprises passing the analyte over the surface of the preconcentrator.

Another embodiment of the invention includes a method of manufacturing the preconcentrator comprising the steps of: supplying a substrate; providing passageways through said substrate; coating the top and bottom of said substrate with a conductive material; coating the top of the conductive material and the inside of the passageways with an adsorbent coating using misted chemical deposition. The method may further include the step of attaching electrical leads to said conductive material.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION

Figure 1:
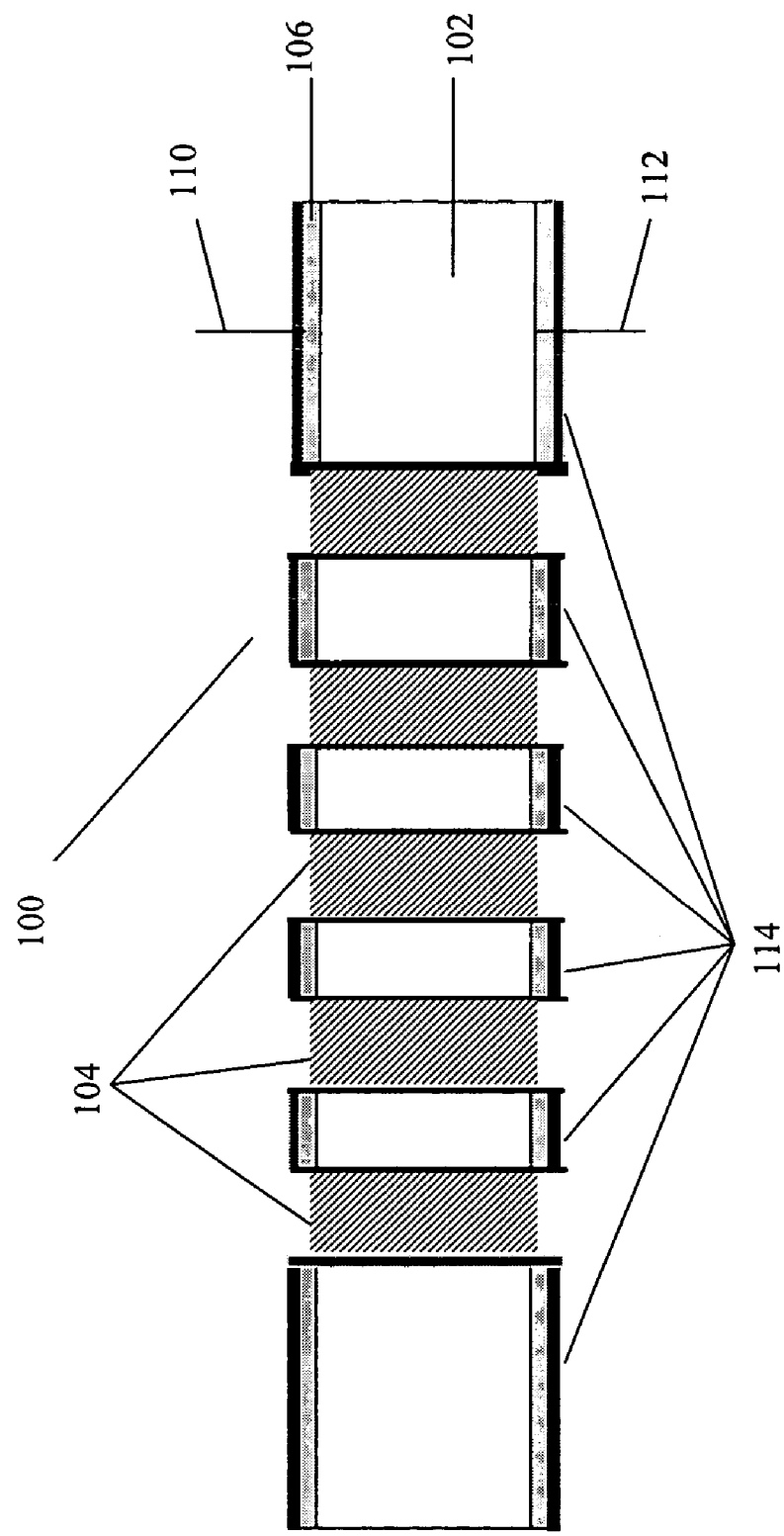
FIG. 1 is a cross-sectional view of a preconcentrator according to an embodiment of the present invention.

Reference will now be made in detail to the preferred embodiments of the present invention, examples of which are illustrated in the accompanying drawings. FIG. 1 is a cross-sectional diagram of a preconcentrator 100 according to an embodiment of the present invention. The preconcentrator 100 includes a substrate 102, illustratively, a rectangular parallelepiped, with passageways 104 running between top and bottom major surfaces, a conductive material 106 covering the top and bottom major surface, except for the passageways, a top electrical lead 110, a bottom electrical lead 112, and an adsorbent coating 114 on the outer surfaces of electrical leads 110, 112. Top electrical lead 110 is connected to conductive material 106 on the top side of the substrate. Bottom electrical lead 112 is connected to conductive material 106 on the bottom side of the substrate. Electrical leads 110, 112 provide for passage of current through the conductive material and substrate so that the entire preconcentrator may be used as a heating element when a voltage is applied across conductive material 106.

Preconcentrator 100 is a three-dimensional preconcentration device with an integral heating element. The preconcentrator may be micro-machined or manufactured using conventional machining and techniques.

The exposed surface area of preconcentrator 100, to which the analyte of interest adsorbs as a sample passes through the preconcentrator, consists of the area at the top and bottom of the substrate 102 as well as on the inside surfaces of passageways 104. Passageways 104 help to maximize this exposed surface area and create a three-dimensional adsorption surface. Thus, preconcentrator 100 has an optimal exposed surface area, a large surface to volume ratio, and an extremely fast preconcentration time. In one preferred embodiment of the invention, the preconcentrator has an increased exposed surface area more than about twenty fold when compared to thin-substrate preconcentrators. In alternate embodiments of the invention, the preconcentrator has an increase in exposed surface area from about two fold to about one hundred fold when compared to thin-substrate preconcentrators.

In another embodiment of the invention, preconcentrator 100 is substantially planar. In an alternate embodiment, the preconcentrator has further surface features that increase the total exposed surface area. Differential etching of the substrate may create such additional surface features.

The preconcentrator may be fabricated in various thicknesses. In one embodiment of the invention, the preconcentrator has a thickness in the range from about 10 microns to about 1000 microns, alternatively from about 20 microns to about 150 microns, alternatively from about 125 microns to about 350 microns, alternatively from about 200 microns to about 600 microns, alternatively from about 450 microns to about 750 microns, alternatively from about 650 microns to about 1000 microns. In an alternate embodiment, the preconcentrator has a thickness from about 1 mm to about 50 mm, alternatively from about 2 mm to about 11 mm, alternatively from about 9 mm to about 20 mm, alternatively from about 15 mm to about 25 mm, alternatively from about 22 mm to about 30 mm, alternatively from about 28 mm to about 39 mm, alternatively from about 37 mm to about 44 mm, alternatively from about 43 mm to about 50 mm. In another embodiment, the preconcentrator has a thickness from about 500 microns to about 1500 microns, alternatively from about 550 microns to about 670 microns, alternatively from about 630 microns to about 760 microns, alternatively from about 740 microns to about 850 microns, alternatively from about 820 microns to about 930 microns, alternatively from about 910 microns to about 1100 microns, alternatively from about 990 microns to about 1120 microns, alternatively from about 1110 microns to about 1240 microns, alternatively from about 1230 microns to about 1390 microns, alternatively from about 1380 microns to about 1450 microns, alternatively from about 1420 microns to about 1500 microns.

Advantageously, particularly for use in portable detectors, a preconcentrator according to the instant disclosure is extremely robust. The structure can be exposed to much higher air pressure, may suffer damage, and remain operable. This robustness is due to substrate 102, which is many times as thick as membrane substrates and extremely rigid thereby creating a firm mounting surface for the preconcentrator.

Substrate 102 may include any material that is rigid, can be micro-machined, and is strong enough to have a conductive material deposited on its surface. This choice of material allows the substrate to remain rigid despite having passageways. To facilitate heating and reduce power consumption, the substrate 102 ideally should not have a large thermal mass. Examples of suitable substrate materials include semiconductor substrates, such as e.g. gallium arsenide or silicon or dielectric materials such as glass, quartz, resins, and plastics. In one embodiment, the substrate is a metal. In another embodiment, the substrate is an SOI wafer. In one embodiment, the substrate is not highly insulating.

The passageways 104 in preconcentrator 100 may take many shapes other than the cylindrical holes shown in FIG. 1. Through use of semiconductor manufacturing techniques, such as deep reactive ion etching, the exact patterning of the passageways 104 can be varied. In another embodiment, the passageways are square holes. In another embodiment, the passageways are slots. In alternate embodiments, the passageways may be serpentine channels.

The large amount of open area in the preconcentrator 100 created by the passageways 104 results in a low-pressure drop across the substrate. This low pressure drop makes the preconcentrator particularly suitable for inline retrofitting to existing detectors for most analytical techniques such as chromatography, mass spectrometry, IMS and field asymmetric ion mobility spectrometry (FAIMS), without altering fluidics or changing existing pumps. Thus, an existing device can be preconcentrating, while operating in a normal detection mode, thereby improving the device's sensitivity. The pressure drop and flow rate related to an interdigitated geometry is given by the following equation:

$$Q = (N \times w \times h^3 \times P)/(12 \times L \times \mu)$$

where: $\mu$ is dynamic viscosity (Air=1.808 $10^{-5}$ N s/m$^2$ at 20° C.)

N is number of drift regions in parallel

L is length of drift region (m)

h is height (m)

w is width of drift region (m)

Q is gas flow (m$^3$/s)

P is pressure (N/m$^2$)

Based on the above equation, one of ordinary skill in the art can determine the appropriate dimensions of a preconcentrator according to the instant disclosure.

Conductive material 106 is a material (e.g. metal) that conducts electricity. Similarly, top electrical lead 110 and bottom electrical lead 112 are made from a conductive material that conducts electricity. Any conductive material known in the art is suitable for the instant disclosure. The conductive material may be, for example, gold, copper, platinum, molybdenum, titanium, chromium, tungsten, or combinations thereof. In one embodiment, the conductive material is a coated Ti barrier layer such as a Ti barrier layer coated with Aluminum.

The electrical leads are connected to a power supply. Any power supply known in the art is suitable for the instant invention. In some applications, the power supply is advantageously a battery as the preconcentrator has low thermal mass. The optimal voltage to be supplied by the power supply depends on the choice of substrate and desired operating parameters. In one embodiment, the power supply applies from about 0.1 volts to about 100 volts, alternatively from about 0.5 volts to about 10 volts, alternatively from about 1 volt to about 15 volts, alternatively from about 10 volts to about 25 volts, alternatively from about 20 volts to about 50 volts, alternatively from about 35 volts to about 80 volts, alternatively from about 55 volts to about 85 volts, alternatively from about 80 volts to about 100 volts the substrate. In another embodiment of the invention, the power supply is a battery.

In one embodiment particularly suitable for FAIMS, the power supply applies from about 0 volts to about 40 volts, alternatively from about 0.1 volts to about 0.5 volts, alternatively from about 0.3 volts to about 1 volt, alternatively from about 0.9 volts to about 10 volts, alternatively from about 9 volts to about 15 volts, alternatively from about 13 volts to about 25 volts, alternatively from about 23 volts to about 35 volts, alternatively from about 30 to about 40 volts.

A voltage applied between the electrical leads causes a current to flow. This current, without being bound by theory, leads to a Joule effect, which heats the preconcentrator, thereby leading to desorption of the analyte. The heating of the device is extremely uniform, as the conductive material creates an integral, continuous, distributed heating element. Furthermore, due to the low thermal mass of the preconcentrator, a low energy input is necessary and heating occurs quickly.

The adsorbent coating 114 covers conductive material 106 and the interior surfaces of passageways 104. By covering the conductive material and interior surfaces, the adsorbent coating causes the heating element to be an internal heating element. This advantageously maximizes heating while minimizing power consumption. The ability of the adsorbent coating to adsorb an analyte of interest depends on chemical selectivity, steric selectivity or both. Adsorbent coatings are commonly known in the art and any such coating may be used In one embodiment of the invention, the adsorbent coating is polydimethylsiloxane (PDMS).

In some embodiments of invention, adsorbent coating 114 selectively adsorbs a plastic explosive or a chemical signature thereof. Thus, the coating may be selective for e.g.

nitroglycerine (NG), dinitrotoulene (DNT), trinitrotoluene (TNT), pentaerythritoltetranitrate (PETN), cyclotrimethylenetrinitramine (RDX), trinitrophenyl-n-methylnitramine (Tetryl), or volatile taggant compounds such 2,3-dimethyl-2,3-dinitrobutane (DMNB) or mononitrotoluene. In other embodiments, the adsorbent is selective for a nerve agent such as dimethyl methyl phosphonate (DMMP).

In other embodiments of the invention, the adsorbent coating selectively adsorbs an illicit drug or a chemical signature thereof. For example, the coating may be selective for mono- and diterpenes released by marijuana, heroin, cocaine, or methamphetamines.

Analytes desorb from the adsorbent coating at different temperatures, highly dependent on the adsorption layer. Thus, by cycling through a series of desorption temperatures it is possible to desorb different classes of analyte over time. Such cycling improves the selectivity and reduces the effects of interferants. In one embodiment of the invention, the adsorbent coating is selective for two or more analytes of interest, which desorb at different temperatures.

In one embodiment, the substrate is coated with one adsorbent coating. In another embodiment, the preconcentrator is coated with more than one adsorbent coating. When the preconcentrator is coated with more than one adsorbent coating, the coatings are applied in such a way that each coating occupies a unique area of the preconcentrator.

In another embodiment of the invention particularly suitable for heating the inlet stream that passes to the detector, the preconcentrator lacks an adsorbent coating.

In an alternate embodiment of the invention, the adsorbent coating has a thickness from about 0.001 microns to about 1 micron, alternatively from about 0.01 microns to about 0.1 microns, alternatively from about 0.05 microns to about 0.3 microns, alternatively from about 0.2 microns to about 0.6 microns, alternatively from about 0.5 microns to about 1 micron. In another embodiment of the invention, the adsorbent coating has a thickness of about 1 micron to about 10 microns, alternatively from about 2 microns to about 7 microns, alternatively from about 5 microns to about 10 microns.

Figure 2:
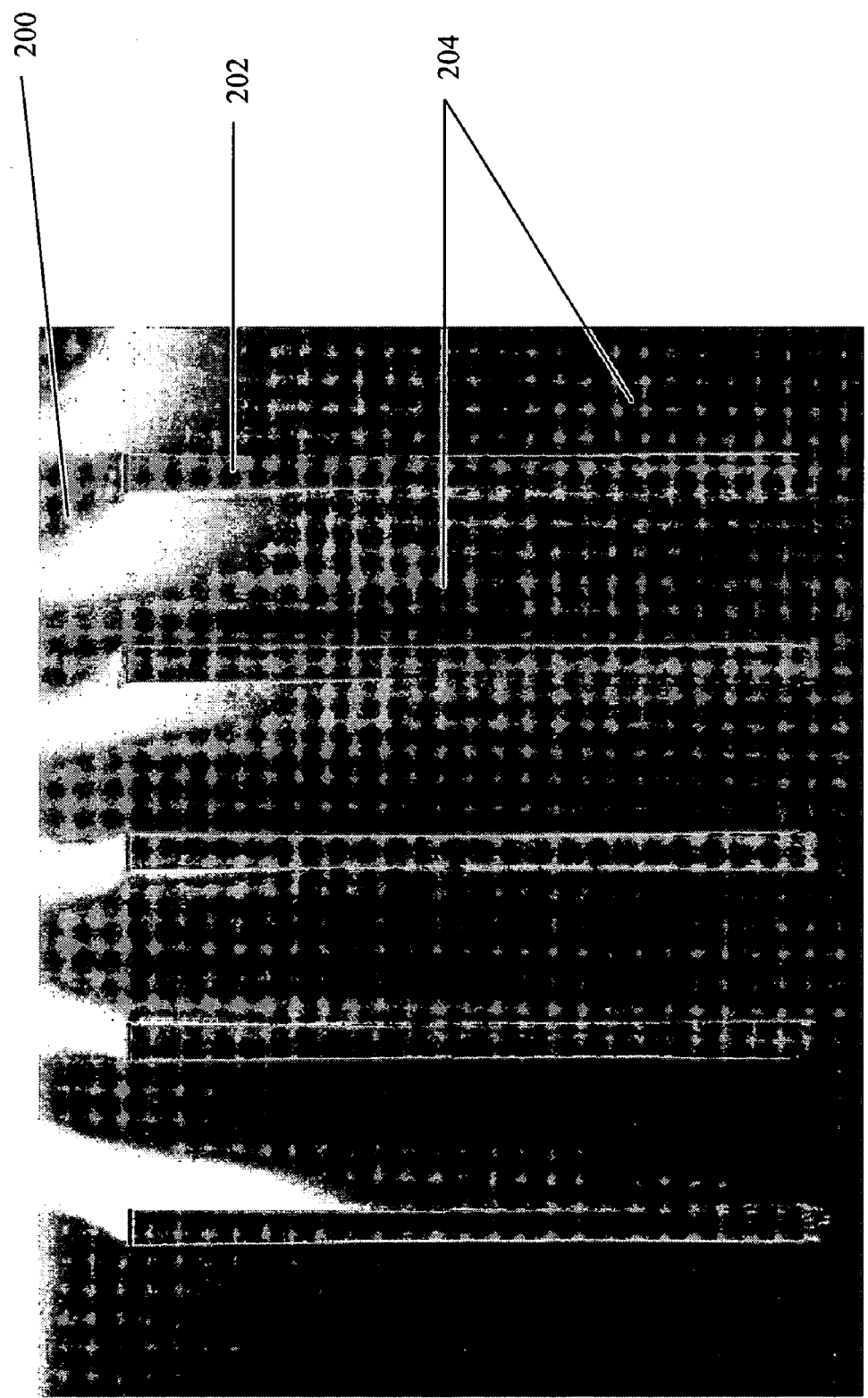
FIG. 2 is an electron micrograph of a cross-section of a preconcentrator according to one embodiment of the present invention.

FIG. 2 is a cross-sectional electron micrograph of the preconcentrator according to one embodiment of the invention. As shown in FIG. 2, preconcentrator 200 is a layered substrate 202 with passageways 204. The layered substrate 202 includes a substrate with a conductive material coating on the top and bottom and an adsorbent coating on the entire surface. In this embodiment of the invention, the passageways 204 are slots. FIG. 2 illustrates how the slotted passageways in the substrate of the present invention create a large surface area to which an analyte can adsorb.

Figure 3:
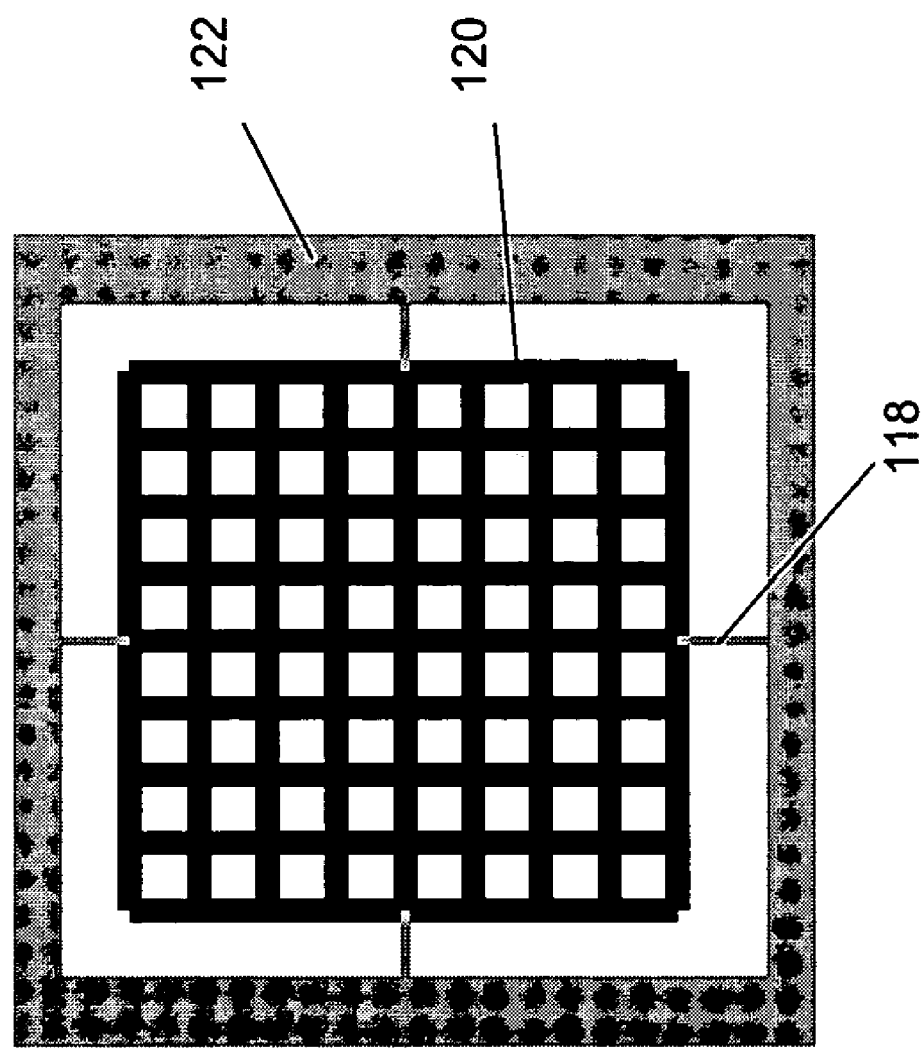
FIG. 3 is a perspective view of a preconcentrator according to one embodiment of the invention.

FIG. 3 is a perspective view of a preconcentrator according to one embodiment of the invention. A connecting bridge 118 connect the coated substrate 120 to a holding frame 122. The coated substrate 120 includes passageways therethrough, a conductive material coating on the top and bottom of the substrate, electrical leads, and an adsorbent coating covering the top of the conductive material and the inside surface of the passageways.

The connecting bridge 118 suspends coated substrate 120 in the holding frame 122. The connecting bridge 118 is thin so as to reduce heat loss to the holding frame, thereby maximizing the effect of heating the substrate and lowering power consumption. In one embodiment, at least two connecting bridges suspend coated substrate 120. In another embodiment, only one connecting bridge suspends the coated substrate. In an alternate embodiment, at least four connecting bridges suspend the coated substrate in the holding frame.

Holding frame 122 separates the analyte adsorbing area of the preconcentrator from the rest of the device. Thus, holding frame 122 and connecting bridge 118 thermally isolate the coated substrate 120 from the surrounding device. This allows the heating to be maximized and reduce power consumption.

The holding frame 122 and connecting bridge 118 may be made from any material that is rigid and can be micromachined. Advantageously, holding frame 122 and connecting bridge 118 have a low thermal mass to further increase the device's efficiency. Examples of such materials include semiconductor substrates, such as e.g. gallium arsenide or silicon or dielectric materials such as e.g. glass, quartz, resins, or plastics.

In an alternate embodiment of the invention, two or more coated substrates are suspended within one holding frame. Each coated substrate contains a substrate, passageways therethrough, conductive material covering the top and bottom, adsorbent coating, and electrical leads as disclosed herein. By using several coated substrates, it is possible to use different adsorbent coatings with preferential selectivity for different analytes. Such coated substrates are connected to each other and the holding frame by connecting bridges. Each coated substrate can be individually addressed electrically to cause heating. The thin connecting bridges provide thermal insulation thereby allowing independent operation. When a holding frame is arranged in such a way, a detection array is created. In one embodiment of the invention, the coated substrate contains a semiconductor substrate. In another embodiment, the coated substrate contains silicon. In an alternate embodiment, each coated substrate in the array has an adsorbent coating selective for a plastic explosive.

Figure 4:
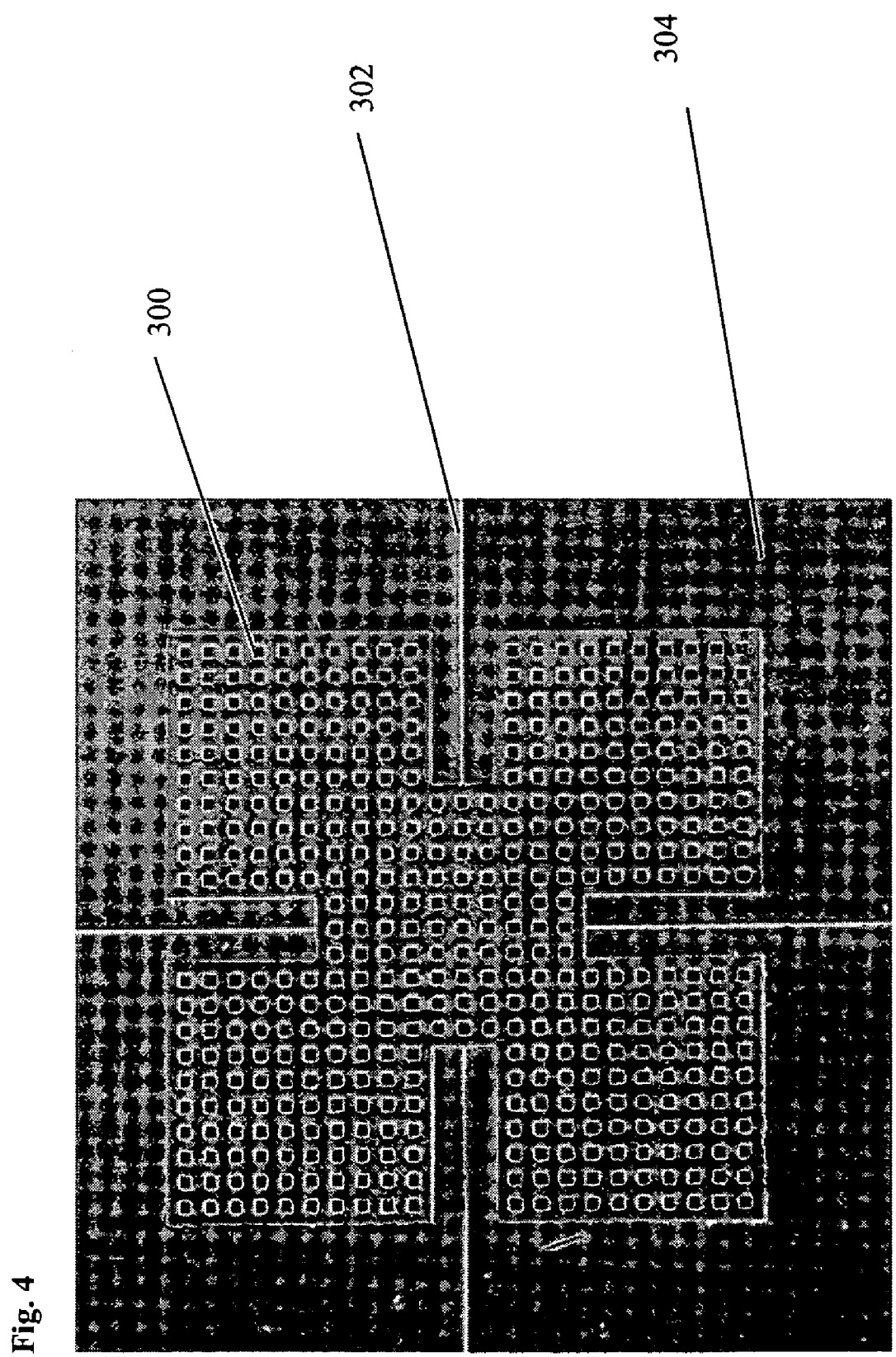
FIG. 4 is a scanning electron micrograph of a preconcentrator according to one embodiment of the invention.

FIG. 4 is a scanning electron micrograph of one embodiment of the preconcentrator according to the invention. Clearly visible is the deeply etched structure of preconcentrator 300 and four thin silicon connecting bridges 302. Also visible is silicon substrate 304. The device of FIG. 4 is incomplete. Prior to use, the remaining silicon substrate 304 would be machined away such that a gas stream could pass through the device.

For temperature sensing, a temperature variable thin-film resistor may be patterned onto the coated substrate. The resistance of this thin film structure changes with temperature. The temperature of the preconcentrator can be determined by measuring the resistance, thereby providing a measurement for closed loop control of the heated preconcentrator. In one embodiment of the invention, the preconcentrator further contains a single thin-film resistor. In another embodiment, the preconcentrator contains a plurality (i.e., more than one) of thin-film resistors. The advantage of using a plurality of resistors is to ensure temperature uniformity and build in redundancy. Alternatively, the preconcentrator may lack a thin-film resistor.

Use of a thin-film resistor enables closed loop operation. Thus, a proportional-integral-differential (PID) controller can be used to accurately control the preconcentrator temperature. The circuit formed by a thin-film resistor and controller can be directly mounted on the ceramic mount upon which the silicon die is fixed. In an alternate embodiment, the preconcentrator contains a plurality of thin-film resistors and a proportional-integral-differential (PID) controller.

As previously discussed, the passageways in the preconcentrator may advantageously create a low-pressure drop across the preconcentrator, which makes it particularly suitable to retrofit to existing detection systems. For retrofitting, it may be desirable to mount a preconcentrator on a support, which is cheaper to produce than the preconcentrator substrate, such that the preconcentrator is properly placed inline with the existing detector. A plurality of preconcentrators may be mounted on a support and attached inline of an existing detector. The support may contain structural polymers such as TEFLON(®), ceramic or polyetheretherketone (PEEK). In one embodiment, the support may be of a standard size with an adapter created for an existing device. Thus, the same design of preconcentrator can be used with many different detectors, only requiring a change in the attachment adapter.

Figure 5:
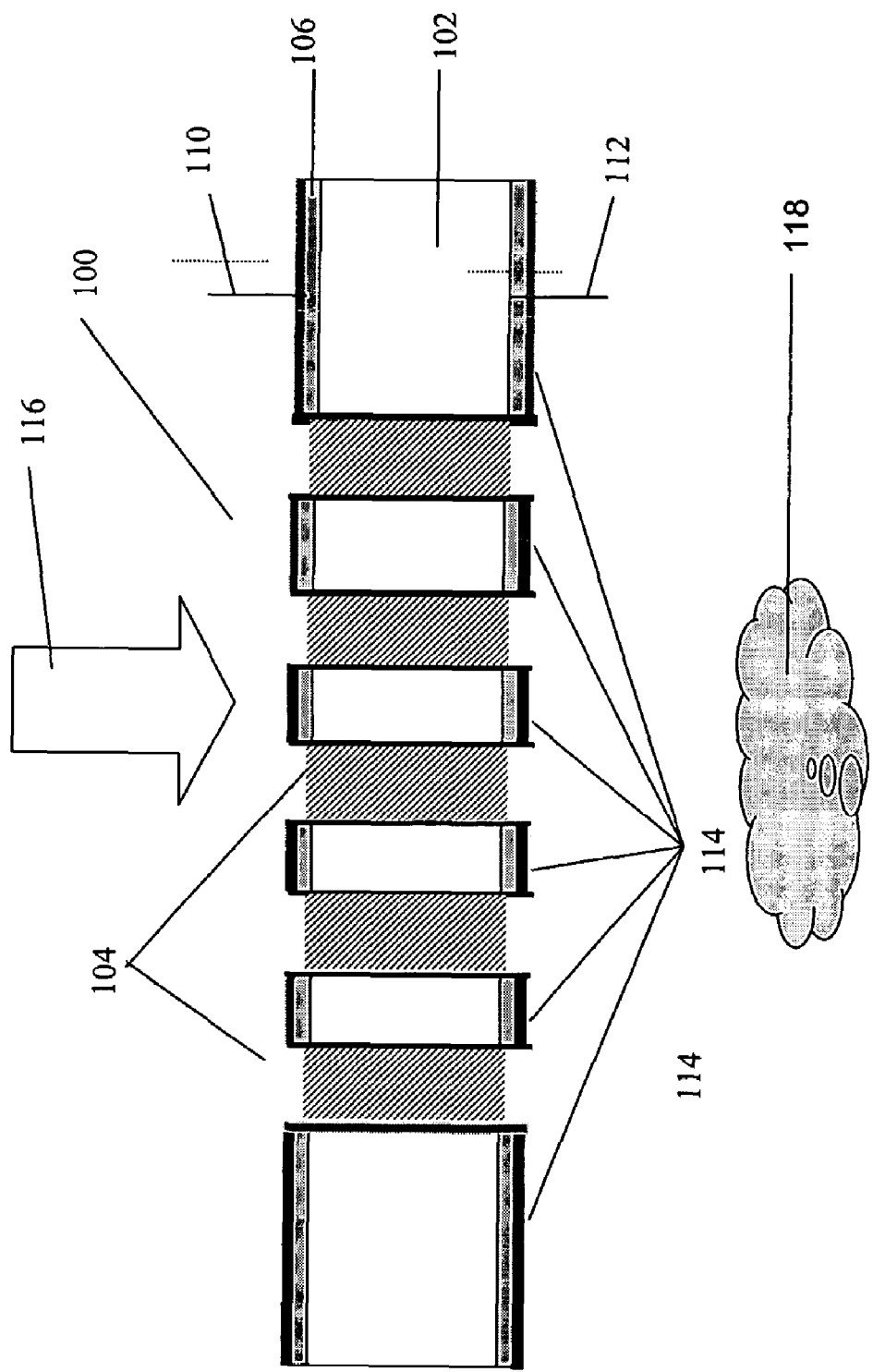
FIG. 5 is a cross-sectional view of the preconcentrator shown in FIG. 1 and illustrates a method of using the preconcentrator according to one embodiment of the present invention.

FIG. 5 illustrates the method of using the preconcentrator of FIG. 1. As described with reference to FIG. 1, the preconcentrator 100 encompasses substrate 102 with passageways 104 therethrough, conductive material 106, top electrical lead 110, bottom electrical lead 112, and adsorbent coating 114. Arrow 116 indicates the flow of the analyte through the three-dimensional structure from the top to the bottom. After the analyte is flowed through the preconcentrator and adsorbed for a predetermined preconcentration time, the structure is heated to release an analyte plume 118 into a detector. The method of using the preconcentrator comprises the steps of (a) contacting the analyte with the adsorbent coating; (b) allowing the analyte to adsorb onto the adsorbent coating; and (c) heating the preconcentrator after a determined period of time to release the concentrated plume of analyte into the detector. In one embodiment, the step of contacting is achieved by flowing gas through the top of the preconcentrator with the flow exiting through the bottom. The step of heating the preconcentrator is achieved by applying a voltage across the electrical leads and allowing, without being bound by theory, the Joule effect to heat the device.

In an alternate embodiment, the method further includes monitoring the temperature of the preconcentrator to ensure that the analyte of interest is released. In that embodiment, the preconcentrator contains at least one thin-film resistor and a proportional-integral-differential (PID) controller.

In another embodiment, the preconcentrator contains an adsorbent coating that adsorbs two or more analytes of interest, which desorb at different temperatures. In that embodiment, the step of heating the preconcentrator further includes cycling the preconcentrator at the temperatures at which the analytes of interest desorb.

As is well known in the art, only certain classes of analytes adsorb onto the adsorbent coating. This property combined with changing the initial air flow can be used to improve the selectivity and reduce the occurrence of false positives. In one embodiment of the invention, a preconcentrator is mounted inline of a detector, with an initial sample stream passing parallel to and over the preconcentrator, but not through it. As the analyte of interest adsorbs to the preconcentrator, interferants are not adsorbed and continue on their path out of the device without ever contacting the inline detector. After a defined preconcentration period, a stream of air is directed to pass through the preconcentrator and the analyte of interest is desorbed from the concentrator stream into the stream that leads to the inline detector. This particular embodiment is especially useful in military warfare agent detectors, when the adsorbent coating selectively adsorbs nerve agents. In a warfare environment, diesel, gasoline and jet fuels all cause significant false alarms when testing for nerve agents.

The preconcentrator according to the instant disclosure can be used for many detectors. The preconcentrator is useful for any detection technique that can benefit from use of a preconcentrator. In one embodiment, the preconcentrator is used inline for IMS. In another embodiment, the preconcentrator is used inline for FAIMS. In another embodiment, the preconcentrator is used inline for gas chromatography. In another embodiment, the preconcentrator is used inline for mass spectrometry.

Standard IMS typically involves heating of the analyte to make the system more robust against environmental variation. Heating is also desirable to prevent analytes from sticking to the apparatus before they reach the detector. The intrinsic heating ability of a preconcentrator according to the instant structure can be used to heat the analyte for IMS. Such inline heating is much more efficient as more of the analyte is heated. The surface area in contact with the flow is much greater allowing for greater heat transfer. In one embodiment of the invention, a preconcentrator according the instant invention is used as an inline heater for standard IMS. In another embodiment, a preconcentrator lacking an adsorbent coating is used as an inline heater for standard IMS.

The three-dimensional structure of a preconcentrator according to the instant disclosure complicates preconcentrator manufacture. The three-dimensional features need to be coated with the adsorbent coating. In some embodiments, the layer is uniform. Thus, special manufacture techniques are required. One technique suitable for applying is liquid source misted chemical deposition. Misted chemical deposition converts a liquid source material into a very fine mist. Nitrogen then carries this mist to a deposition chamber. In the deposition chamber, sub-micron droplets coalesce on the wafer thereby covering it with a uniform liquid film. This film is then thermally cured leaving a thin surface layer of solid. Thus, this technique allows for a uniform coating of a three-dimensional structure. One embodiment of the invention is a method of manufacturing of a preconcentrator comprising the steps of: a. supplying a substrate; b. providing passageways through said substrate; c. coating the top and bottom of said substrate with a conductive material; d. coating the entire substrate with adsorbent coating using misted chemical deposition. The method may further include the step of attaching electrical leads to the conductive material.

In one embodiment of the invention, the mist deposited has a droplet size from about 0.1 microns to about 0.3 microns, alternatively from about 0.15 microns to about 0.27 microns. In another embodiment, the method further includes the step of mounting the substrate in a holding frame.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A preconcentrator comprising:

a substrate with passageways therethrough;

a conductive material covering the top and bottom of the substrate;
a top electrical lead connected to the conductive material covering the top of the substrate;
a bottom electrical lead connected to the conductive material covering the bottom of the substrate;
an adsorbent coating on top of the conductive material and along the inside of the passageways.

2. The preconcentrator of claim 1, wherein the substrate comprises silicon.

3. The preconcentrator of claim 1, wherein the conductive material comprises a Ti barrier layer coated with Aluminium.

4. The preconcentrator of claim 1, wherein the adsorbent comprises polydimethylsiloxane.

5. The preconcentrator of claim 1 further comprising;
a holding frame; and
a connecting bridge connecting the substrate to the holding frame.

6. The preconcentrator of claim 5, wherein the holding frame and the connecting bridge comprises silicon.

7. The preconcentrator of claim 1, wherein the preconcentrator is placed inline with a detector.

8. The preconcentrator of claim 1, further comprising a temperature variable thin-film resistor.

9. The preconcentrator of claim 8, further comprising a temperature-controlling proportional-integral-differential controller.

10. The preconcentrator of claim 1, further comprising a support.

11. The preconcentrator of claim 10 wherein the support is selected from the group consisting of polytetrafluoroethylene, ceramic or polyetheretherketone.

12. An array preconcentrator comprising:
two or more preconcentrators, each preconcentrator comprising:
a substrate with passageways therethrough,
a conductive material covering the top and bottom of the substrate,
a top electrical lead connected to the conductive material covering the top of the substrate,
a bottom electrical lead connected to the conductive material covering the bottom of the substrate, and
an adsorbent coating on top of the conductive material and along the inside of the passageways.

13. The array preconcentrator of claim 12, wherein each preconcentrator selectively adsorbs a different analyte of interest.

14. The array preconcentrator of claim 12 further comprising
a holding frame; and
a connecting bridge connecting each preconcentrator to the other and to the holding frame.

15. The array preconcentrator of claim 14, wherein the substrate, holding frame and connecting bridge comprise silicon.

16. A method of preconcentrating analyte comprising:
i) contacting the analyte and a preconcentrator wherein the preconcentrator comprises:
a substrate with passageways therethrough;
a conductive material covering the top and bottom of the substrate;
a top electrical lead connected to the conductive material covering the top of the substrate;
a bottom electrical lead connected to the conductive material covering the bottom of the substrate; and
an adsorbent coating on top of the conductive material and along the inside of the passageways;
ii) adsorbing the analyte to the adsorbent coating at a temperature and for a period sufficient to allow the analyte to adsorb; and
iii) releasing the analyte from the adsorbent coating.

17. The method of claim 16 wherein the preconcentrator is inline with a detector.

18. The method of claim 17 wherein the step of contacting the analyte with a preconcentrator comprises passing the analyte over the surface of the preconcentrator.

19. The method of claim 16 wherein the substrate comprises silicon.

20. The method of claim 19 wherein the preconcentrator further comprises a temperature variable thin-film resistor.

21. The method of claim 19 further comprising a temperature-controlling proportional-integral-differential controller.

22. The method of claim 16 wherein the step of releasing the analyte comprises heating the adsorbent coating to a temperature at which the analyte desorbs.

23. A method of manufacturing of a preconcentrator comprising the steps of:
i) supplying a substrate;
ii) providing passageways through said substrate;
iii) coating the top and bottom of said substrate with a conductive material;
iv) coating the top of the conductive material and the inside of the passageways with an adsorbent coating using misted chemical deposition.

24. The method of claim 23 further comprising attaching electrical leads to said conductive material.

25. A preconcentrator for heating an inlet comprising:
a substrate with passageways therethrough;
a conductive material covering the top and bottom of the substrate;
a top electrical lead connected to the conductive material covering the top of the substrate; and
a bottom electrical lead connected to the conductive material covering the bottom of the substrate.

26. The preconcentrator of claim 25, wherein the preconcentrator is placed inline with a detector.

* * * * *